United States Patent [19]
Hickok et al.

[11] Patent Number: 5,839,896
[45] Date of Patent: Nov. 24, 1998

[54] DENTAL POST EXTRACTOR APPARATUS

[75] Inventors: Teresa R. Hickok, Bonita; Clifford J. Ruddle, Santa Barbara, both of Calif.

[73] Assignee: San Diego Swiss Machining, Inc., Chula Vista, Calif.

[21] Appl. No.: 44,115

[22] Filed: Mar. 19, 1998

[51] Int. Cl.⁶ ...................................................... A61C 3/14
[52] U.S. Cl. ............................................ 433/159; 433/152
[58] Field of Search .................................. 433/152, 158, 433/159, 160

[56] References Cited

U.S. PATENT DOCUMENTS

| | | | |
|---|---|---|---|
| 1,102,850 | 7/1914 | Arden | 433/152 |
| 2,181,746 | 11/1939 | Siebrandt | 433/159 |
| 2,541,357 | 2/1951 | Hersh | 433/160 |
| 4,443,196 | 4/1984 | Rico | 433/158 |
| 5,015,185 | 5/1991 | Cane et al. | 433/159 |

*Primary Examiner*—John J. Wilson
*Attorney, Agent, or Firm*—Baker & Maxham

[57] ABSTRACT

A dental tool apparatus for use in the removal of a dental post and other intercanal obstructions comprises a pliers having a first end for mounting a post connector and a second end for applying a force to the connector a substantially elongate post connector defined by a shaft having a proximal for attachment to a lever device, and a distal end having an open bore having a stepped diameter and self taping threads in the bore at the end for engaging and threading onto a dental post.

20 Claims, 3 Drawing Sheets

DENTAL POST EXTRACTOR APPARATUS

BACKGROUND OF THE INVENTION

This invention relates generally to dental tools and pertains more particularly to a special dental removal system for radicular posts/dowels and other intercanal obstructions.

It is common practice in dentistry to place a post and core within an endodontically treated tooth to mechanically enhance the retention of a dental restoration. First the root canal system is cleaned, shaped, and obturated, followed by creating a specific preparation within a root canal for the subsequent placement of a particular post type. The selected post is then seated and retained by cement or adhesives. A dental restoration is subsequently fabricated and cemented or bonded over the post, core and remaining prepared tooth structures. Posts can be fabricated or selected in a variety of geometrical configurations and dental materials. Generally, post-types include parallel, tapered (screw or cast configurations), or fiber posts. Posts vary according to length, diameter, shape, head configurations, and are further selected according to stock versus custom. Post materials utilized range from precious and nonprecious metals to non-metallic posts, such as the new carbon fiber varieties. Furthermore, posts are placed and then retained by reliable cements and new generation, highly retentive bonding agents. In any event, over time, many endodontic cases fail necessitating post removal to facilitate endodontic retreatment procedures and/or prosthetic rehabilitation.

In the past, post removal has been difficult due to lack of effective tools for the task. Historically the procedures for post removal included drilling, vibrating with rotosonics or ultrasonics instruments, or utilizing awkward devices that posed significant limitations and typically sacrificed great amounts of tooth structure; hence, predisposing the root to perforation or subsequent fracture. The aforementioned techniques were employed until the post was loosened and removed. Certain post types and cementing materials retain posts so securely that the techniques described are either unsuccessful, time consuming, or aggressively predispose to irreversible root damage and the loss of the tooth. Finally, the technical inability to remove a post, or perceived inability, has led to countless surgical procedures.

Therefore, there is a need for an improved dental removal system that can be utilized for the safe and effective elimination of dental posts/dowels and other intercanal obstructions.

SUMMARY OF THE INVENTION

A primary objective of this invention is to provide a significantly improved dental removal system for radicular posts/dowels and other intercanal obstructions.

In accordance with a primary aspect of the present invention a dental tool apparatus for use in the removal of a dental post comprises the combination of a pliers having a first end for mounting a post connector and a second end having means for applying a force to said connector, a substantially elongated post connector defined by a shaft having a proximal end with attachment means at said proximal end for attachment to a lever device, and a distal end having an open bore with a stepped diameter and self taping threads in said bore at said end for engaging and threading onto a dental post.

BRIEF DESCRIPTION OF DRAWING

The objects, features and advantages of this invention will be more readily appreciated from the following detailed description, when read in conjunction with the accompanying drawing, in which.

DETAILED DESCRIPTION OF PREFERRED EMBODIMENTS

Figure 1:
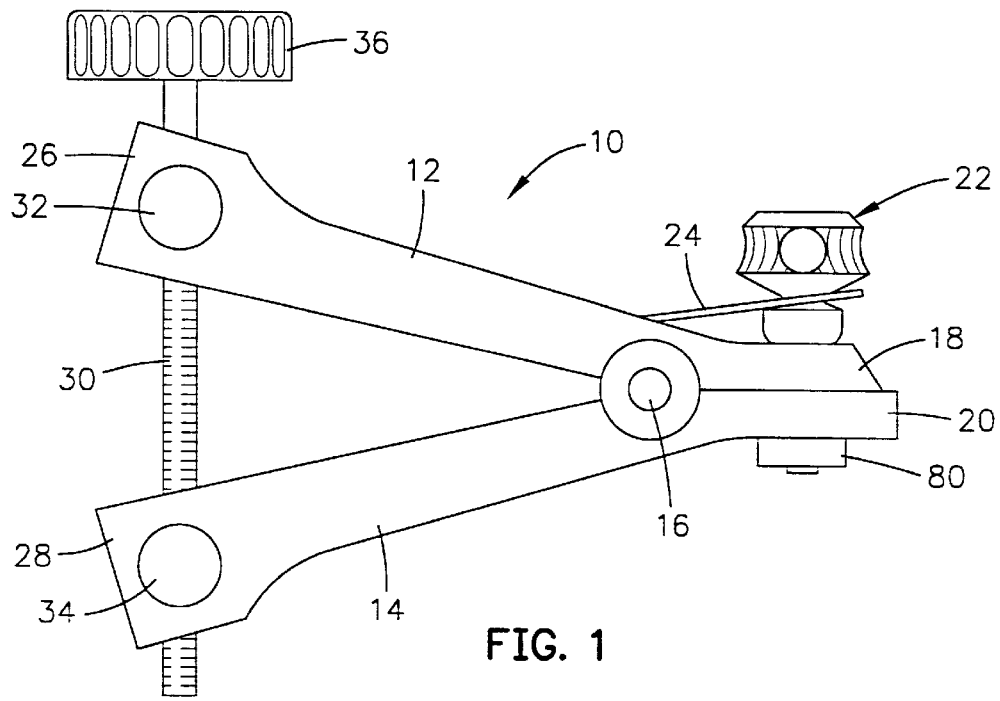
FIG. 1 is a side elevation view of the dental removal system in accordance with an exemplary embodiment of the invention.

The present invention is directed to and concerns an improved dental removal system for the safe and effective removal of dental posts and other interadicular obstructions. The apparatus is described with reference to preferred embodiments of the invention as illustrated in the drawings. While this invention is described in terms of the best mode for achieving this invention's objectives, it will be appreciated by those skilled in the art that variations may be made in view of these teachings without deviating from the spirit or scope of the invention.

Referring to FIG. 1 of the drawings there is illustrated an exemplary embodiment of an apparatus for removal of dental posts and other intercanal obstructions, in accordance with the present invention, designated generally by the numeral 10. The illustrated apparatus comprises a tubular tap for engaging a post or other canal obstructions, a protective cushion, and an extracting plier. The pliers comprises upper and lower levers 12 and 14 pivotally connected together at a pivot pin 16 so that both levers are on opposite sides of the pivot point. With this connection arrangement, when the ends of the levers on one side of the pivot point are brought together by the screw knob, the opposite end of the levers move apart. This provides a leveraging or separating force as opposed to a gripping force.

The extracting pliers lever units each have a first or connecting end 18 and 20 having provision, such as a bore or slot for receipt of the tubular tap 22 which connects to a post or other intercanal obstruction. The extracting plier is used to mount on the tubular tap and the screw knob applies a leveraged extraction force to a post in a tooth root as will be hereinafter described. A spring latch or retainer member 24 is attached at one end to the upper lever 12 and at the other end secures or holds the tubular tap connector 22 in place within the extracting plier unit.

The extracting pliers levers each have a second end 26 and 28 which is on the longer of the arms of each lever and are used as will be described for force input. An elongated screw 30 is connected between the second ends 26 and 28 of the levers 12 and 14 and functions to pull the second ends of the levers together to spread the first ends 18 and 20 apart and apply force to the tubular tap connector 22. The screw 30 is rotatably mounted in a bore in a plug or pin member 32 at the outer end of the upper lever 12 and is threadably engaged in a threaded bore in a nut 34 in the lower outer end 28. A turning knob or handwheel 36 is mounted on the upper end of the screw 30 to enable finger or hand application of torque to the screw to rotate it and draw the outer ends 26 and 28 of the levers 12 and 14 together and forcing the connecting ends apart.

Figure 2:
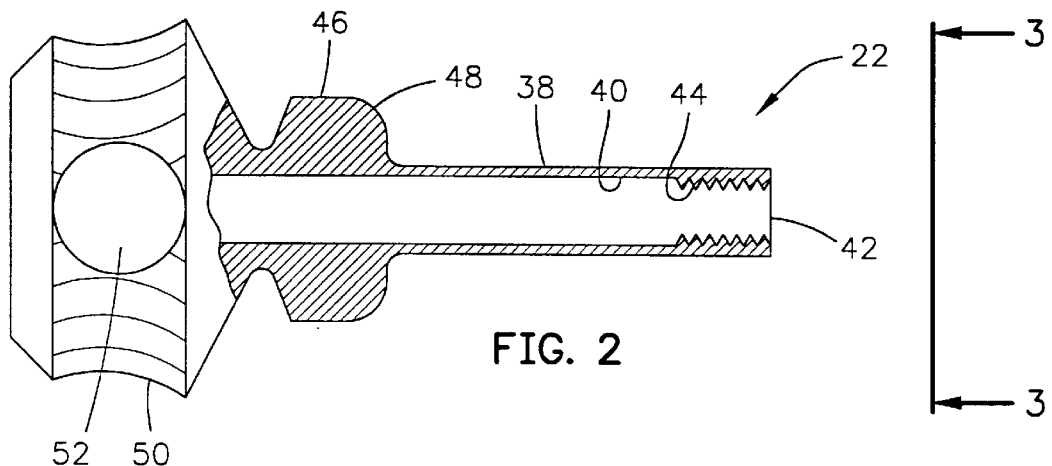
FIG. 2 is an enlarged view of the tubular tap connecting device of the dental removal system of FIG. 1.
Figure 3:
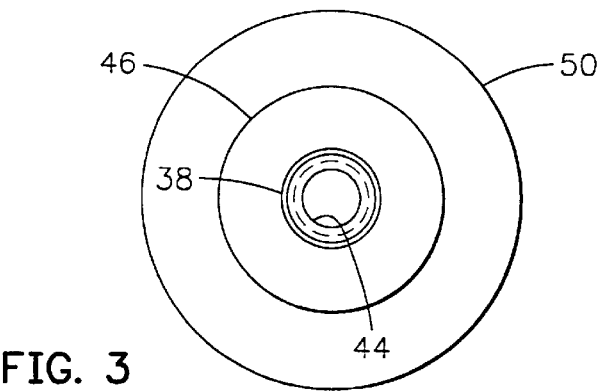
FIG. 3 is a view taken on line 3—3 of FIG. 2.

Referring to FIG. 2, the tubular tap connector 22 is illustrated and comprises an elongated tubular shaft 38 having a bore 40 with an open end 42 with tapping or cutting threads 44 at the open end. The bore is formed with a smaller diameter at the open end for threads 44 with a larger diameter extending from the threads to substantially the other end of the shaft 38. The outer surface of the shaft is formed with an enlarged diameter portion 46 having a rounded bearing portion 48 for engagement with the connecting end 18 of the upper lever 12 of the extracting plier. An enlarged head 50 is formed as a thumb wheel with a knurled surface to grasp and rotate the connector to thread it onto an end of a post. A plurality of cross bores (only one shown) 52 are formed in the thumb wheel for receiving a handle in the form of a rod for applying torque to enhance rotational efficiency of the tubular tap connector.

Figure 7:
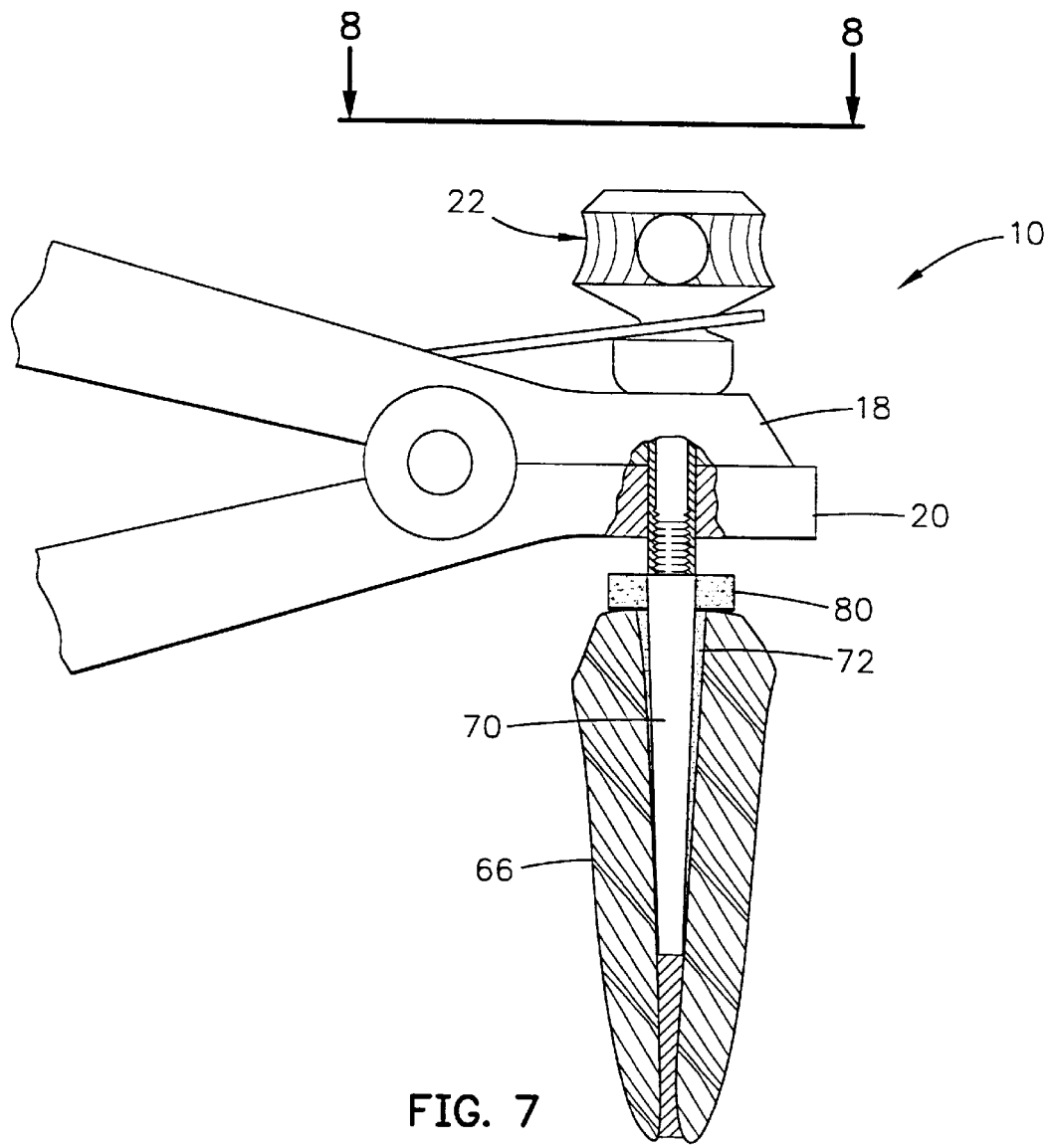
FIG. 7 is a view like FIG. 6 showing the removal system of FIG. 1 in position to initiate extrication forces required to remove the posts.

The tubular tap connector is designed to thread onto the coronal most end of a dental post or other intercanal obstruction as will be subsequently discussed with respect to FIG. 7. The threads 44 are self taping, that is they cut or form threads on the post or any other intercanal obstructions as the engaged tubular tap head is rotated. The tubular tap is threaded, engaged and connected to the post or intercanal obstruction which enables removal tension to be utilized during the extricating process.

Figure 4:
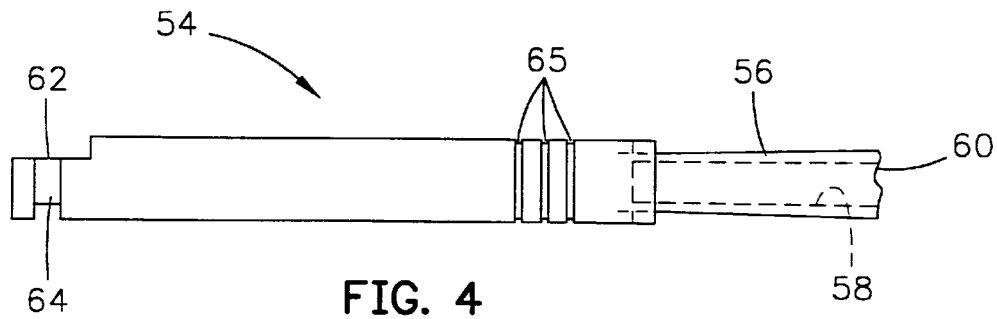
FIG. 4 is a side elevation view of the trephine used for machining the coronal most aspect of the exposed intercanal obstruction.

Referring to FIG. 4, a trephine in the form of a coring mandrel or hollow drill is illustrated and designated generally by the number 56. This tool comprises an elongated cylindrical body 54 having a tubular cutting tip or end 56. The cutting end 56 is an elongated tubular section having a bore 58 for receiving a dental post or other intercanal obstruction and an annular or peripheral set of cutting teeth 60 for cutting and machining down the most coronal aspect of the post or other type of obstruction. The drill 56 is formed with a tool connector head comprising a flat 62 and a groove 64 for mating with a suitable slow-speed handpiece for rotating the drill for the cutting and machining the coronal most aspect of the post or other obstruction. The trephine drill is provided with one or more indicia rings 65 for identifying a specific drill unit size.

Figure 5:
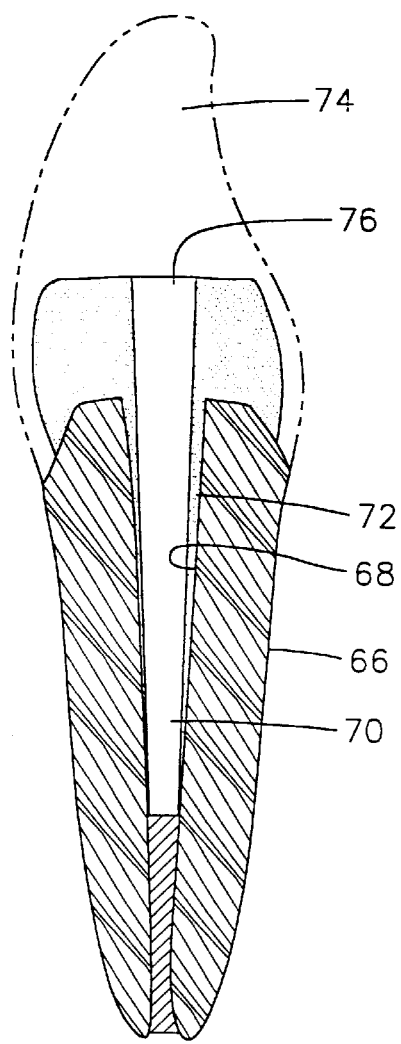
FIG. 5 is a side elevation view of a tooth with a post cemented in place.

Referring to FIG. 5, the natural tooth's root is illustrated at 66 having an internal cavity or root canal 68 in which has been mounted a post 70 retained by cement or a bonding agent 72. A prosthetic crown 74 is seated on the prepared natural root/crown and is anchored to the post 70 and post head 76 with cement or bonding agent. The post head 76 is typically embedded in the prosthetic crown or build-up core material.

Figure 6:
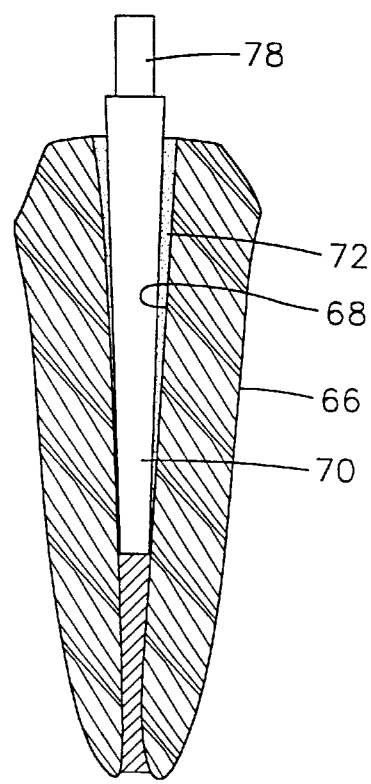
FIG. 6 is a view like FIG. 5 showing the prosthetic crown and core removed, and the coronal most part of the post exposed and machined-down utilizing a specific trephine.

Referring to FIG. 6, the prosthetic crown 74 has been removed and the coronal cement/core 72 has been eliminated exposing the post head 76. The post 70 has a post head 76 which is machined down coronally 78 creating a round specifically sized cylinder. The post head 76 is machined-down at 78 utilizing a tool called a trephine 54 illustrated in FIG. 4. The trephine 54 is positioned such that its cutting edge 60 engages the post head 76 and rotated so the post head 76 is machined down at 78. This action results in forming a round cylinder, as illustrated in FIG. 6 for receiving a tubular tap. The working end 42 of the tubular tap connector 22 is fitted over the rounded cylinder 78 and screwed on and drawn-down over the coronal most end of the post 70. Specific dental burs and/or ultrasonic instruments are used to remove circumferential tooth structure or restorations from around the post or other intercanal obstructions. A specifically sized tool 54 will machine down and size the post head 76 so a correspondingly sized tubular tap 22 can be selected and engage a post or other intercanal obstruction.

The post head 76 is engaged by the open end 42 of the connector 22, such that the threads 44 engage and cut or form threads in the post as the connector is rotated. As soon as the connector has been rotated sufficiently to form a secure connections over a portion of the coronal end of the post 70, the extracting plier may then be activated to pull the tubular tap connector upward with respect to the natural tooth root 66 and thereby pulls the post or obstruction from the root canal 68. A cushion 80 of sufficient diameter protects the natural tooth or prosthetics by evenly distributing the removal loads over the biting surface of the tooth. The extracting pliers lower lever 20 pushes down on the bumper cushion 80 and protects the tooth as illustrated in FIG. 7. Thereafter, the hand knob 36 is rotated, thereby rotating screw 30 so that the outer ends 26 and 28 of the pliers levers are drawn together thereby spreading the levers or jaws 18 and 20. This pulls the tubular tap connector 22 engaging the post 70 which is cemented or bonded 72 from the root canal 68.

Figure 8:
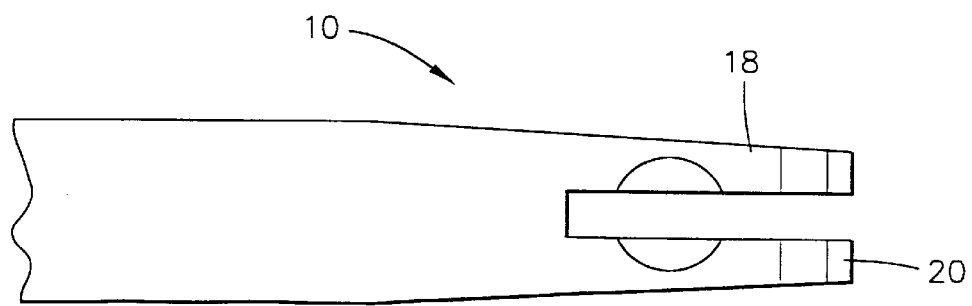
FIG. 8 is a top plan view of the connecting end of the extracting plier.

Referring to FIG. 8, a top view of the connector end of the extracting plier is illustrated showing a slot 80 through the levers for receiving the tubular tap connector 22. A scalloped recess 82 in the top of the upper lever receives and engages the rounded portion 48 of the connector.

In summary, an exemplary embodiment of a dental removal system for posts/dowels and other obstructions or kit in accordance with the present invention, comprises a Domer Bur, 5 trephines and 5 correspondingly sized tubular taps, variably sized protective cushions, a torque pin, and an extracting plier. Clinically, root canal obstructions can have their coronal ends modified and rounded with the Domer Bur which helps guide the subsequently used instruments. Specifically, post heads can be altered to precise diameters with any particular trephine so a correspondingly sized tubular tap can be rotated to form threads, engage and be drawn down over a particular obstruction.

The extracting plier is mounted to the engaged tubular tap. The extracting plier has two jaws that can progressively open and are controlled by turning the screw knob. As the extracting plier jaws open, force is exerted on the engaged tubular tap as the knob is turned until the obstruction is loosened and removed. Some obstructions can be engaged and removed by just trephines and/or tubular taps without utilizing the extracting plier. Additionally, certain other obstructions can be extracted by using only the extracting plier in conjunction with existing dental and medical instruments other than trephines and tubular taps.

The present post removal system is best employed when ultrasonic efforts are not successful. The post removal system requires that all pulp chamber restorative materials circumferential to the post be removed. These materials include composite, amalgam, bonding agents, and cements.

In the case where a tap strips off the post, a sequentially smaller tap can be used or the procedure restarted again using a smaller trephine bur and corresponding tap.

Cast cores must be reduced in size with high speed burs until a diameter is created slightly larger than dimensions of the interradicular dowel. Caution must be exercised to not over reduce the head of the post which could prevent engaging the post with the smallest tap. The trephine burs should be used on the same axis as the post to prevent over-reduction. If a thin incisal edge of an anterior tooth is encountered, it can be reduced to increase the surface flatness and better distribute the removal loads. Modified wooden tongue depressors can be placed on the incisal edges of adjacent teeth to better distribute and dampen the removal loads.

The extracting plier should never be used on a screw post as its threads typically are engaging lateral dentin and a fractured root is likely to occur. The Domer Bur is used to round off the coronal most aspect of the post. This is important as it guides and directs the trephine and tap over the post and along its axis.

The preferred procedure is to select the largest trephine possible that will just engage the post. Using a high torque, low speed handpiece set in a clockwise direction, drill down over the coronal most aspect of the post approximately three millimeters. Select a silicone cushion of adequate size such that it will not be displaced into the access cavity and will distribute the post removal loads over the biting surface of the tooth evenly. Select the tap corresponding to the trephine size and insert the silicone cushion onto this instrument.

Place the tap onto the coronal most aspect of the rounded post and firmly push in an apical direction, screwing it onto the post with a counter-clockwise rotation. Ideally, the tap should be threaded down over the post approximately three millimeters. Once the tap securely engages the post, the torque pin can be inserted through the head of the tap for added leverage on larger posts, or used to rotate the tap counter-clockwise to unscrew a threaded post. Push the silicone cushion down so it contacts and protects the tooth.

Orient the pliers to the extracting jaws engage the tap. When correctly inserted, one jaw will be against the cushion and the opposing jaw is under the outcropping on the tap. The tubular top's thin metal retention flange is between the outcropping and tap handle.

Holding the Remover firmly with one hand, use the free hand to turn the screw knob clockwise which will open the jaws. As the jaws begin to open, make certain the cushion is properly protecting the tooth. Continue turning the screw know until post loosens and can be removed. If resistance is encountered, a CPR 1 ultrasonic instrument can be held on the tap to encourage post retention failure and allow the knob to be progressively turned.

While we have illustrated and described our invention by means of specific embodiments, it is to be understood that numerous changes and modifications may be made therein without departing from the spirit and the scope of the invention as defined in the appended claims.

We claim:

1. A dental tool apparatus for use in the removal of a dental post, the apparatus comprising in combination:
    a pliers defined by a pair of pivotally connected levers having a first end for mounting a post connector and a second end having means for applying a force to said connector;
    a substantially elongate post connector defined by a shaft having a proximal end with attachment means at said proximal end for attachment to a lever device, and a distal end having an open bore having a stepped diameter and self taping threads in said bore at said end for engaging and threading onto a dental post.

2. The apparatus of claim 1, wherein said attachment means is a rounded shoulder.

3. The apparatus of claim 2, wherein said proximal end includes a knob for grasping with a hand for manipulating.

4. The apparatus of claim 2, wherein said proximal end includes at least one cross bore for receiving a handle for applying torque to said tool.

5. The apparatus of claim 1, wherein said proximal end includes at least one cross bore for receiving a handle for applying torque to said tool.

6. The apparatus of claim 5, wherein said pliers includes a rotatable threaded shaft connected between said second ends of said levers, and means for rotation of said shaft for pulling said distal ends of said levers toward one another.

7. The apparatus of claim 1, wherein said pliers includes a rotatable threaded shaft connected between said second ends of said levers, and means for rotation of said shaft for pulling said distal ends of said levers toward one another.

8. The apparatus of claim 7, wherein said stepped diameter includes a first diameter portion which includes said self taping threads.

9. The apparatus of claim 8, wherein said proximal end includes a knob for grasping with a hand for manipulating.

10. The apparatus of claim 9, wherein said proximal end includes at least one cross bore for receiving a handle for applying torque to said tool.

11. The apparatus of claim 7, wherein said proximal end includes at least one cross bore for receiving a handle for applying torque to said tool.

12. The apparatus of claim 11 wherein said pliers comprises first and second levers each having a proximal end and a distal end, said levers pivotally connected together intermediate said ends, said proximal ends having means for mounting said connector whereby one of said proximal ends engage a tooth and the other proximal end engage a shoulder on a tool to thereby pull said tool away from said tooth.

13. The apparatus of claim 12 further comprising a hollow drill for removing cement from around a post.

14. The apparatus of claim 1 wherein said pliers comprises first and second levers each having a proximal end and a distal end, said levers pivotally connected together intermediate said ends, said proximal ends having means for mounting said connector whereby one of said proximal ends engage a tooth and the other proximal end engage a shoulder on a tool to thereby pull said tool away from said tooth.

15. The apparatus of claims 14 wherein said pliers includes a rotatable threaded shaft connected between said distal ends of said levers, and means for rotation of said shaft for pulling said distal ends of said levers toward one another.

16. A dental threading tool for use in combination with dental pliers for the removal of a dental post, the tool comprising:
    a substantially elongate tool defined by a shaft having a proximal end with attachment means at said proximal end for attachment to a lever device, and a distal end having an open bore having a stepped diameter and self taping threads in said bore at said end for engaging and threading onto a dental post.

17. The tool of claim 16, further comprising dental pliers comprising first and second levers each having a proximal end and a distal end, said levers pivotally connected together intermediate said ends, said proximal ends having means for mounting said tool whereby one of said proximal ends engage a tooth and the other proximal end engage a shoulder on a tool to thereby pull said tool away from said tooth.

18. The tool of claim 17, wherein said pliers includes a rotatable threaded shaft connected between said distal ends of said levers, and means for rotation of said shaft for pulling said distal ends of said levers toward one another.

19. The apparatus of claim 16, wherein said pliers includes a rotatable threaded shaft connected between said distal ends of said levers, and means for rotation of said shaft for pulling said distal ends of said levers toward one another.

20. The apparatus of claim 19, wherein said stepped diameter includes a first diameter portion that includes said self taping threads.

* * * * *